(12) United States Patent
Proctor Beauchamp et al.

(10) Patent No.: US 11,410,755 B2
(45) Date of Patent: Aug. 9, 2022

(54) COMPUTER-BASED SYSTEM FOR PROVIDING PSYCHOLOGICAL THERAPY

(71) Applicant: IESO Digital Health Limited, Cambridgeshire (GB)

(72) Inventors: Guy James Proctor Beauchamp, Cambridgeshire (GB); Ann Gail Hayes, Cambridgeshire (GB); Barnaby Adam Perks, Cambridgeshire (GB); Sarah Elisabeth Bateup, Cambridgeshire (GB)

(73) Assignee: IESO Digital Health Limited, Cambridgeshire (GB)

( * ) Notice: Subject to any disclaimer, the term of this patent is extended or adjusted under 35 U.S.C. 154(b) by 580 days.

(21) Appl. No.: 15/524,803

(22) PCT Filed: Nov. 6, 2014

(86) PCT No.: PCT/GB2014/053312
§ 371 (c)(1),
(2) Date: May 5, 2017

(87) PCT Pub. No.: WO2016/071660
PCT Pub. Date: May 12, 2016

(65) Prior Publication Data
US 2018/0308574 A1    Oct. 25, 2018

(51) Int. Cl.
*G16H 10/60* (2018.01)
*G16H 50/30* (2018.01)
(Continued)

(52) U.S. Cl.
CPC .............. *G16H 10/60* (2018.01); *G16H 10/20* (2018.01); *G16H 20/70* (2018.01); *G16H 40/67* (2018.01);
(Continued)

(58) Field of Classification Search
CPC ........ G06Q 30/00; G06Q 50/22; G06Q 30/06; G06Q 10/1097; G06Q 30/02; G06Q 50/01;
(Continued)

(56) References Cited

U.S. PATENT DOCUMENTS

2003/0059750 A1    3/2003  Bindler et al.
2008/0046292 A1    2/2008  Myers et al.
(Continued)

FOREIGN PATENT DOCUMENTS

AU    2003204909 A1    1/2004
WO    2016071660 A1    5/2016

OTHER PUBLICATIONS

International Search Report received in corresponding PCT Application PCT/GB2014/053312, dated Jun. 12, 2015.
(Continued)

*Primary Examiner* — Michael Tomaszewski
*Assistant Examiner* — William T. Monticello
(74) *Attorney, Agent, or Firm* — Vorys, Sater, Seymour and Pease LLP

(57) ABSTRACT

Apparatus for use in a computer-based system for providing psychological therapy, the apparatus comprising: an access system configured to control access to features and data by users of remote devices, wherein the users comprise patients, therapists and supervisors; and a therapy system configured to enable text-based instant messages to be sent between patients and therapists; wherein the access system is configured to allow patients to retrieve messages sent and received by the patient, therapists to retrieve messages sent and received by the therapist, and supervisors to retrieve messages sent and received by particular patients and/or therapists.

13 Claims, 6 Drawing Sheets

(51) Int. Cl.
*G16H 40/67* (2018.01)
*G16H 50/70* (2018.01)
*G16H 10/20* (2018.01)
*G16H 20/70* (2018.01)
*G16H 80/00* (2018.01)

(52) U.S. Cl.
CPC .............. *G16H 50/30* (2018.01); *G16H 50/70* (2018.01); *G16H 80/00* (2018.01)

(58) Field of Classification Search
CPC ........ G06Q 50/00; G06Q 40/00; G06H 10/60; G06F 19/3418; G06F 17/00; G05B 15/02; H04R 3/00; H04L 12/2827; G16H 50/30
See application file for complete search history.

(56) References Cited

U.S. PATENT DOCUMENTS

| | | | |
|---|---|---|---|
| 2011/0078564 A1* | 3/2011 | Almodovar-Herraiz et al. | |
| 2011/0105854 A1* | 5/2011 | Kiani et al. | |
| 2012/0259652 A1* | 10/2012 | Mallon et al. | |
| 2012/0320145 A1 | 12/2012 | Kahn | |
| 2013/0275161 A1* | 10/2013 | Dutta et al. | |
| 2013/0325491 A1* | 12/2013 | Ferrari | |
| 2014/0223462 A1* | 8/2014 | Aimone et al. | |
| 2014/0280136 A1* | 9/2014 | Marshall et al. | |
| 2015/0052160 A1* | 2/2015 | Hussam | |
| 2015/0302766 A1* | 10/2015 | Oberlander et al. | |
| 2015/0324532 A1* | 11/2015 | Jones et al. | |
| 2015/0370993 A1* | 12/2015 | Moturu et al. | |
| 2016/0022193 A1* | 1/2016 | Rau et al. | |
| 2016/0358284 A1* | 12/2016 | Bagley | |
| 2016/0378928 A1* | 12/2016 | Benton et al. | |
| 2017/0235912 A1* | 8/2017 | Moturu et al. | |
| 2017/0348327 A1* | 12/2017 | Kanes et al. | |

OTHER PUBLICATIONS

Burch et al., The Use of Internet-Enabled Cognitive Behavioral Therapy in the Treatment of Depression and Anxiety amongst Older People, The International Journal of Aging and Society, vol. 8, Issue 1, 2017, Common Ground Research Networks, Champain, IL 61820 USA.

Burch, Preston, Bateup, True technology-enabled mental health care: trust, agency and ageing, mHealth, Jun. 21, 2018.

Kessler et al., Therapist-delivered internet psychotherapy for depression in primary care: a randomised controlled trial, Lancet 2009; 374:628-34, Aug. 22, 2009.

* cited by examiner

COMPUTER-BASED SYSTEM FOR PROVIDING PSYCHOLOGICAL THERAPY

FIELD

The present invention relates, amongst other things, to a computer-based system for providing psychological therapy.

BACKGROUND

The provision of psychological therapy via computer-based systems is of interest. This application relates to technical systems and specific methods for providing such therapy in a more effective way.

SUMMARY

According to a first aspect of the present invention, there is provided apparatus for use in a computer-based system for providing psychological therapy, the apparatus comprising:
 an access system configured to control access by users of remote devices to features and data, wherein the users comprise patients, therapists and supervisors; and
 a therapy system configured to enable text-based instant messages to be sent between patients and therapists;
 wherein the access system is configured to allow patients to retrieve messages sent and received by the patient, therapists to retrieve messages sent and received by the therapist, and supervisors to retrieve messages sent and received by particular patients and/or therapists.

Thus, the system can effectively handle large numbers of remote users and can enable effective supervision of patients and/or therapists.

According to a second aspect of the present invention, there is provided a computer-implemented method comprising:
 obtaining text from text-based messages sent between a patient and a therapist providing psychological therapy;
 determining at least one feature of the text; and
 determining a characteristic of the patient and/or the therapist using the at least one feature.

Thus, the method can provide an effective and efficient way of determining characteristics of patients and/or therapists by analysing the text-based messages sent therebetween. This can enable, for example, alerting of particular situations or scenarios of concern.

According to a third aspect of the present invention, there is provided a method of providing psychological therapy, the method comprising:
 a therapist exchanging text-based messages with a remotely situated patient via a computer-based system, wherein the messages comprise instant messages exchanged during sessions; and
 providing a set of between about 5 and 10 sessions and/or a set of sessions with a total duration of between 1.5 and 7.5 hours to achieve a recovery rate of at least about 42% and/or an improvement rate of at least about 59%.

Thus, the method can provide a particularly effective way of providing psychological therapy.

Optional features are specified in the dependent claims.

BRIEF DESCRIPTION OF THE DRAWINGS

Certain embodiments of the present invention will now be described, by way of example only, with reference to the accompanying drawings in which.

DETAILED DESCRIPTION OF THE CERTAIN EMBODIMENTS

System

Figure 1:
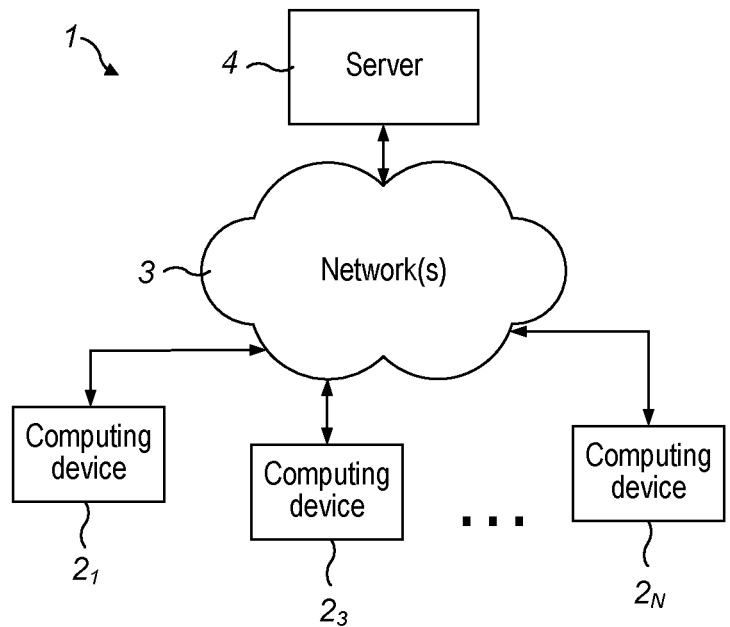
FIG. 1 illustrates a computer-based system for providing psychological therapy.

Referring first to FIG. 1, a computer-based system 1 for providing psychological therapy will now be described. The system 1 includes a number of computing devices 2 connectable, via one or more networks 3, to a server 4. As will be explained in more detail below, the system 1 is configured to enable therapists to provide psychological therapy to patients under the supervision of supervisors, the supervisors, therapists and patients being users of the computing devices 2.

The computing devices 2 may be of any type. The computing devices 2 are preferably configured to run a web browser software application.

The network system 3 preferably includes the Internet.

Figure 2:
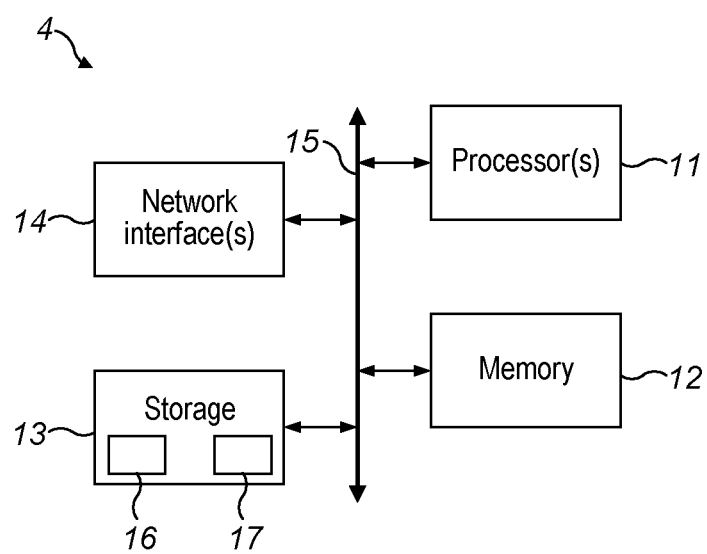
FIG. 2 illustrates hardware of a server included in the system of FIG. 1.

Referring to FIG. 2, the server 4 preferably includes one or more processors 11, memory 12, storage 13, and one or more network interfaces 14, interconnected via a bus 15. The server 4 may include several units as illustrated in FIG. 2 interconnected via a network. The memory 12 includes volatile memory (e.g. dynamic random-access memory) and is used by the processors 11 for temporary data storage. The storage 13 includes non-volatile (non-transitory) memory (e.g. read-only memory, flash memory) and/or storage (e.g. magnetic storage). The storage 13 stores computer-readable instructions 16. When executed, the computer-readable instructions 16 cause the server 4 (or each unit included in the server 4) to (cooperate with one another to) perform the functions described below. The storage 13 also stores data 17 for use by the server 4.

Figure 3:
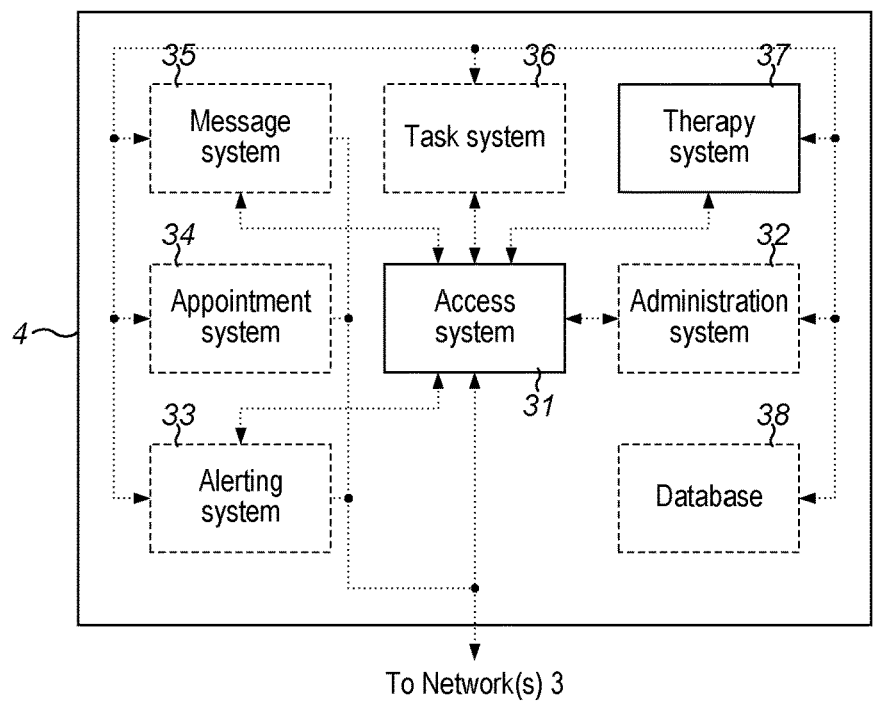
FIG. 3 illustrates systems included in the server of FIG. 2.

Referring to FIG. 3, the server 4 includes several system modules, preferably including an access system 31, an administration system 32, an alerting system 33, an appointment system 34, a messaging system 35, a task system 36, and a therapy system 37. The server 4 also includes a database 38. Each of these elements of the server 4 will be described below.

Figure 4:
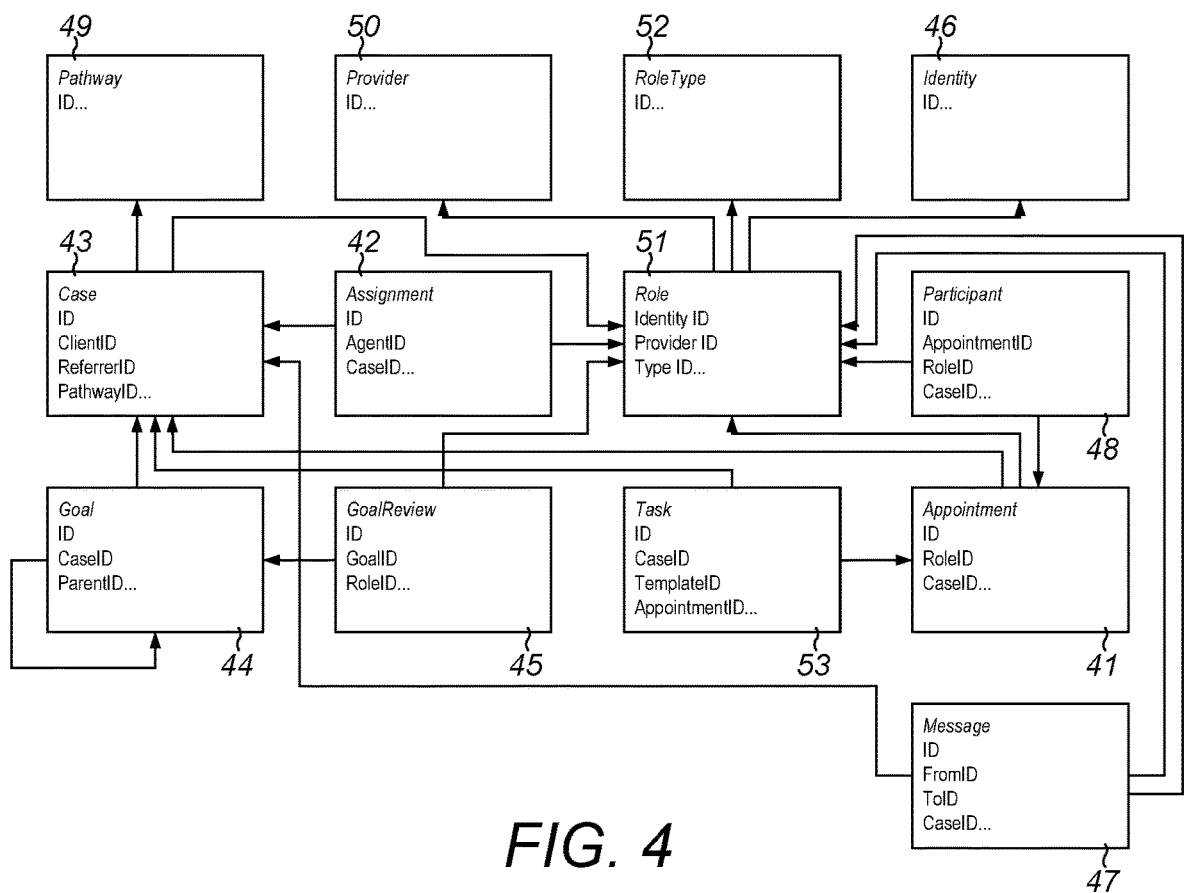
FIG. 4 illustrates a data model used in the server of FIG. 2.

Referring to FIG. 4, the database 38 includes several tables, including, amongst others, an appointment table 41, an assignment table 42, a case table 43, a goal table 44, a goal review table 45, an identity table 46, a message table 47, a participant table 48, a pathway table 49, a provider table 50, a role table 51, a role type table 52, and a task table 53. The figure illustrates associations between tables. Certain of these tables and/or records thereof will be described below.

The access system 31 is configured to control user access to features and data. Preferably, the access system 31 is configured to enable users to log in to the server 4 and to provide an interface (hereinafter referred to as a user interface) that is suitable for each type of user. The user interface preferably corresponds to a web-based user interface. Login information associated with a user is determined by an identity record. Access to features and data is determined by a role record. There are several role types, including patients, therapists, supervisors and administrators.

The administration system 32 is configured to enable administrators to perform various actions e.g. in relation to the database 38. New patient and therapist accounts (identity records) can be created. A role (role record) can be associated with an identity (identity record). One or more cases (case records) can be associated with a patient (role record). A case corresponds to a programme of therapy. A case (case record) is associated with a pathway (pathway record), which determines the programme of therapy that is offered to the patient. A therapist (role record) can be assigned (by way of an assignment record) to a case (case record). Preferably, supervisors can be associated with therapists in a similar way.

The therapy system 37 is configured to enable instant messages to be sent between patients and therapists. The instant messages are text-based, i.e. include text. The instant messages are exchanged during sessions of therapy. The server 4 is preferably configured to provide, via the user interface, an indication of whether or not the other user is online and/or is in the process of typing a new message. Sessions may be ended in any suitable way. A transcript of a session, i.e. the messages sent during the session, is saved in the database 38 (a transcript table is not shown in FIG. 4). The transcripts are preferably encrypted.

The therapy system 37 and/or another element of the server 4 is configured to enable therapists to make notes relating to patients of the therapist and/or to produce other types of documents. The notes and documents are saved in the database 38, preferably encrypted.

The messaging system 35 is configured to enable non-instant messages to be sent between patients and therapists. The non-instant messages are also text-based. Preferably, the non-instant messages can include file attachments. The non-instant messages can be sent at any time, e.g. between sessions. The messaging system 35 is configured to notify patients and therapists, e.g. via email, that they have received a non-instant message. Patients or therapists can log in to the server 4 and view the non-instant message via the user interface. Messages are stored in message records in the database 38, preferably with encrypted contents.

The task system 36 is configured to enable users to set and/or complete tasks. Tasks include various types of activity, including questionnaires and goals. Other tasks include thought records, formulation sheets, behavioural experiment and behavioural experiment record sheets, recordings of mindfulness activities, activity diaries, behavioural activation records, activity schedules, psycho-education, graded hierarchies of fears, records of exposure, therapy blueprints, surveys, responsibility pie charts, etc. In use, tasks are normally set by a therapist and completed by a patient. Suitable user interface elements are provided for these purposes. The task system 36 is configured to determine scores based upon certain completed tasks, e.g. questionnaires (see below). The scores can be used for various functions, as will be explained in more detail below.

The appointment system 34 is configured to enable appointments for sessions to be made. Preferably, the appointments can be created by therapists and need to be accepted by patients. Appointment records are stored in the database 38. The server 4 is configured to provide appointment reminders to patients, e.g. by email and/or short message service (SMS) message.

The alerting system 33 is configured to provide alerts to therapists and/or supervisors in dependence upon particular conditions. The conditions may include that that the data relating to a task completed by a patient meets one or more particular criteria. Alerts can be provided in any suitable way, e.g. by email or via the user interface provided by the server 4 to the therapist or supervisor.

In some examples, an alert can be provided in response to a score determined from a questionnaire completed by a patient indicating that a level of a psychological condition of the patient is above a particular threshold. For example, a PHQ-9 score and/or GAD-7 score (see below) of 15 or above indicating severe depression and/or anxiety, respectively, may trigger such an alert. Such an alert is preferably provided to a therapist of the patient and/or to a supervisor of the therapist.

In some examples, an alert can be provided in response to two or more scores determined from questionnaires completed by a patient at different times indicating that there is insufficient improvement in a level of a psychological condition of the patient.

In some examples, an alert can be provided in response to data relating to one or more patients of a therapist indicating that the therapist is not performing sufficiently well. Such data may relate to scores determined from questionnaires, recovery or improvement data (see below) determined from the scores, patients not attending sessions, patients dropping out of therapy, etc. Such an alert is preferably provided to a supervisor of the therapist.

As mentioned above, the access system 31 is configured to control user access to features and data.

In particular, the access system 31 is configured to allow patients to retrieve messages sent and received by the patient, therapists to retrieve messages sent and received by the therapist, and supervisors to retrieve messages sent and received by particular patients and/or therapists.

Preferably, the access system 31 is also configured to allow patients to retrieve data relating to tasks completed by the patient, therapists to retrieve data relating to tasks completed by patients of the therapist, and supervisors to retrieve data relating to tasks completed by particular patients and/or patients of particular therapists.

Preferably, the access system 31 is also configured to allow therapists to retrieve notes relating to patients of the therapist and supervisors to retrieve notes relating to particular patients and/or patients of particular therapists.

Figure 5:
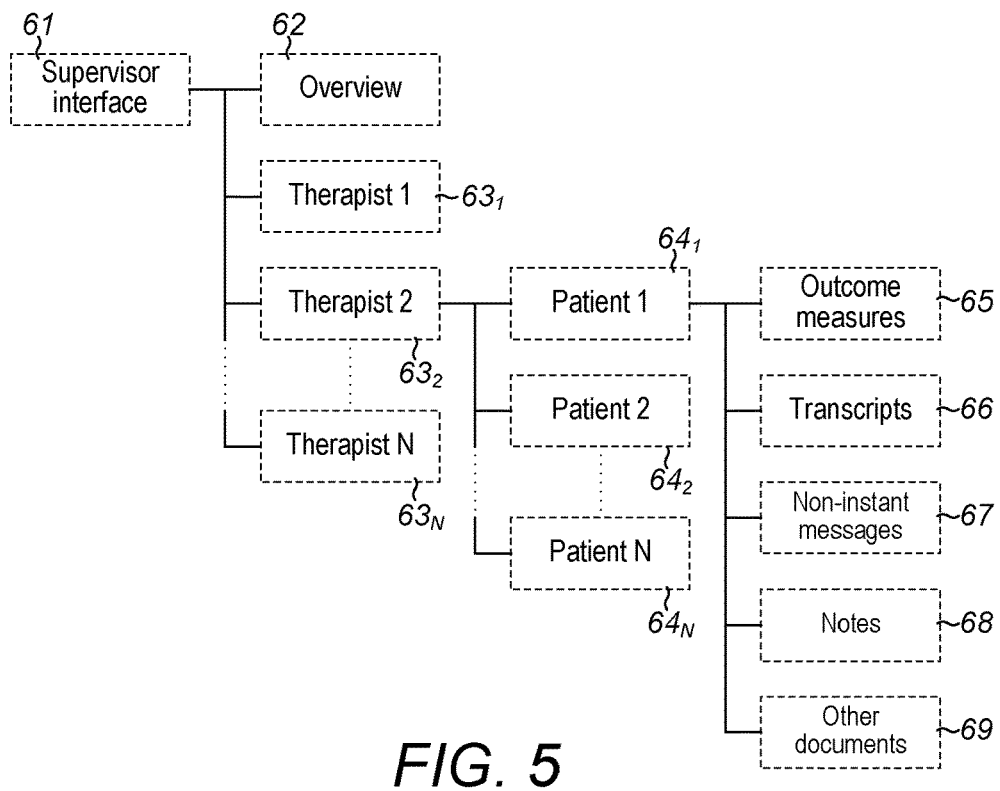
FIG. 5 illustrates a structure of a user interface provided to a supervisor by the server of FIG. 2.

Referring to FIG. 5, an example of a user interface 61 (hereinafter referred to as a supervisor interface) provided by the access system 31 will now be described. The supervisor interface 61 is provided to a supervisor after logging in as described above. The supervisor interface 61 includes several elements. Only one element may be provided at one time, or multiple elements may be provided. The elements preferably include an overview element 62 and one or more therapist elements 63. There is preferably a therapist element 63 for each therapist associated with the supervisor. Each therapist element 63 includes one or more patient elements 64. There is preferably a patient element 64 for each patient of each therapist associated with the supervisor (only one set of which is illustrated in the figure). Each patient element 64 includes an outcome measures element 65, a transcripts element 66, a non-instant messages element 67, a notes element 68, and an other documents element 69 (only one set of which is illustrated in the figure).

The overview element 62 provides a representation of data relating to all of the therapists associated with the supervisor. The data may include e.g. averages of recovery data (see below), improvement data (see below), non-attendance data and drop-out data for patients of the therapists. The therapists may be ranked in dependence upon this data.

A therapist element 63 enables access to the relevant patient elements 64. A patient element enables access to the remaining elements 65, 66, 67, 68, 69.

The outcome measures element 65 provides a representation of outcome measures, e.g. scores determined from questionnaires, etc. These may be represented as a function of time. The transcripts element 66 enables viewing of the transcripts associated with the patient. The non-instant messages element 67 enables viewing of the non-instant messages sent or received by the patient. The notes element 68 enables viewing of the notes made by the therapist and relating to the patient. The other documents element 69 enables viewing of any other documents relating to the patient. This data is retrieved from the database 38 as appropriate.

Thus, the supervisor can effectively supervise psychological therapy provided by therapists to patients.

The user interface (hereinafter referred to as the therapist interface) provided to a therapist preferably includes some of the same elements as the supervisor interface 61. In particular, the therapist interface preferably include a patient element 64 for each patient of the therapist. Each patient element 64 preferably includes the same elements 65, 66, 67, 68, 69 as in the supervisor interface 61.

The user interface (hereinafter referred to as the patient interface) provided to a patient also preferably includes some of the same elements as the supervisor interface 61. In particular, the patient interface preferably includes at least a transcripts element 66 and a non-instant messages element 67.

Second Type of Server

Figure 6:
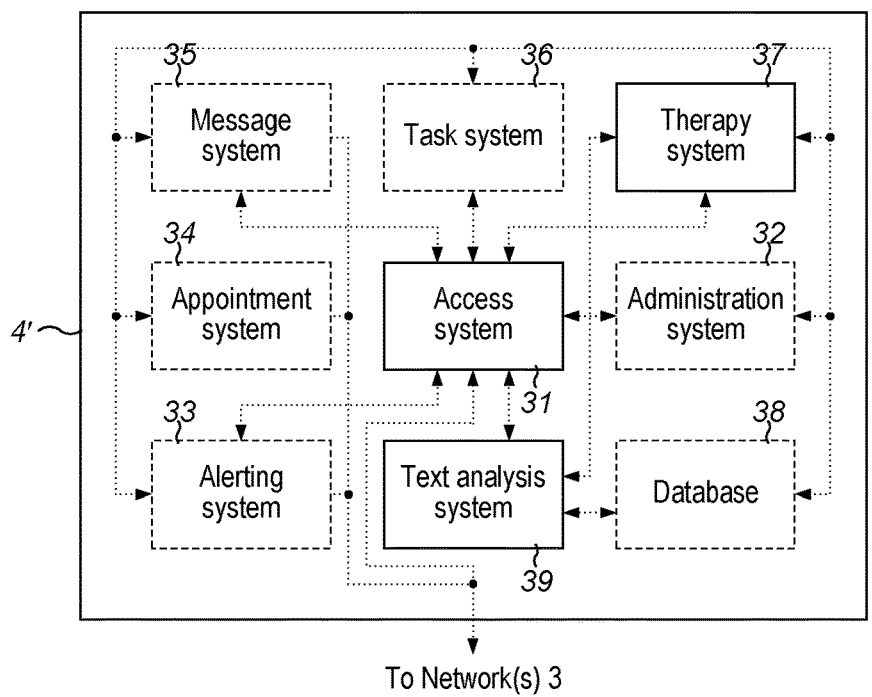
FIG. 6 illustrates a second type of server that may be included in the system of FIG. 1.
Figure 7:
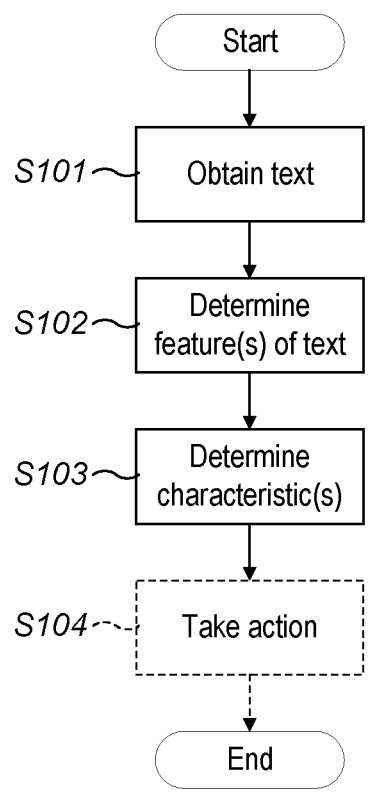
FIG. 7 illustrates a method that may be performed by the server of FIG. 6.

Referring to FIG. 6, a second type of server 4' (hereinafter referred to as the second server) will now be described. The second server 4' preferably has all of the above described features of the server 4. The second server 4' preferably also includes a text analysis system 39. As will be explained in more detail below, the text analysis system 39 is configured to obtain text from messages sent between patients and therapists, determine at least one feature of the text, and determine a characteristic of a patient and/or a therapist using the at least one feature.

Method of Analysing Text

Referring to FIG. 6, a method that can be performed by the second server 4' will now be described.

At a first step S101, the text analysis system 39 obtains text from text-based messages sent between a patient and a therapist.

The text may be obtained from messages sent both by the patient and by the therapist, or from messages sent by the patient only or by the therapist only. The messages may correspond to instant-messages and/or non-instant messages sent as described above. The text may be obtained from any suitable set of messages, e.g. the messages sent during one or more sessions.

The method preferably starts automatically, e.g. periodically and/or after detecting that a new non-instant message or a new transcript has been added to the database 38.

At a second step S102, the text analysis system 39 determines one or more features of the text obtained at the first step S101.

At a third step S103, the text analysis system 39 determines a characteristic of the patient and/or the therapist using the features obtained at the second step S102.

The features and/or the characteristics may be determined in any suitable way. For example, they may be determined by analysing the text using a text mining/analytics process. The text mining process may include one or more of the following actions: information retrieval or identification of a corpus; natural language processing such as part of speech tagging, syntactic parsing, and other types of linguistic analysis; named entity recognition; disambiguation; recognition of pattern identified entities; coreference; relationship, fact, and event extraction; sentiment analysis; quantitative text analysis; etc.

Further data, e.g. data relating to patients, scores, etc. may also be taken into account when determining the features and/or the characteristics.

A characteristic determined at the third step S103 may relate to a predicted outcome of therapy. A characteristic may relate to risky behaviour by the patient. A characteristic may relate to a predicted drop-out by the patient. A characteristic may relate to performance of the therapist.

At an optional fourth step S104, the second server 4' takes an action. This may involve the alerting system 33 providing an alert to a therapist and/or supervisor in dependence upon the determined characteristics. For example, an alert can be provided if the characteristic is determined to have a value that corresponds to a situation or scenario of concern. Alerts can be provided in any suitable way, e.g. by email or via the therapist interface or supervisor interface 61. The second server 4' may store the characteristics.

Method of Providing Psychological Therapy

Figure 8:
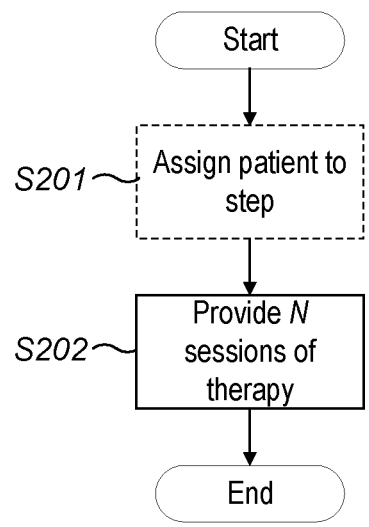
FIG. 8 illustrates a method of providing psychological therapy that can be performed using the system of FIG. 1.

Referring to FIG. 8, a method of providing psychological therapy, particularly cognitive behavioural therapy (CBT), will now be described.

At an optional first step S201, a patient is assigned to a step of a stepped care model e.g. by a therapist (see below).

At a second step S202, the method involves a therapist exchanging text-based messages with a remotely situated patient via a computer-based system. The messages comprise instant messages exchanged during sessions. The sessions preferably have a duration of between about 0.5 and 1 hour. The computer-based system is preferably a system 1 as described above with reference to FIG. 1 etc.

As will be explained below, the method can provide a particularly effective way of providing psychological therapy.

The second step S202 preferably comprises providing a set of between about 5 and 10 sessions and/or a set of sessions with a total duration of between 1.5 and 7.5 hours to achieve a recovery rate of at least about 42% and/or an improvement rate of at least about 59%.

Recovery rate corresponds to a percentage of patients that are recovered at the end of the set of sessions. Recovery preferably corresponds to a patient having a PHQ-9 score (see below) of less than 10 and/or a GAD-7 score (see below) of less than 8. This can be referred to as statistically reliable recovery.

Improvement rate corresponds to a percentage of patients that are improved at the end of the set of sessions. Improvement preferably corresponds to a patient having a PHQ-9 score that has decreased by at least 6 and/or a GAD-7 score that has decreased by at least 4 since before the set of sessions. This can be referred to as statistically reliable improvement.

For patients having mild depression and/or anxiety, e.g. patients at step 2 of a stepped care model, the second step S202 preferably comprises providing a set of about 5 sessions and/or a set of sessions having a total duration of between 1.5 and 2.5 hours to achieve a recovery rate of at least about 76% and/or an improvement rate of at least about 54%.

For patients having moderate depression and/or anxiety, e.g. patients at step 3 of a stepped care model, the second step S202 preferably comprises providing a set of about 7 sessions and/or a set of sessions having a total duration of between 4 and 6.5 hours to achieve a recovery rate of at least about 33% and/or an improvement rate of at least about 60%.

For patients having (moderately) severe depression and/or severe anxiety, e.g. patients at step 3+ of a stepped care model, the second step S202 preferably comprises providing a set of about 10 sessions and/or a set of sessions having a total duration of between 6.5 and 7.5 hours, thereby achieving a recovery rate of at least about 40% and/or an improvement rate of at least about 60%.

Depression severity is preferably defined with reference to a PHQ-9 score and/or anxiety severity with reference to a GAD-7 score (see below).

Patient Health Questionnaire (PHQ-9)

PHQ-9 is a nine item self-administered questionnaire that reliably detects the presence/severity of depression. It has been specifically designed for use in primary care. PHQ-9 has demonstrated usefulness as an assessment tool with acceptable, reliability, validity, sensitivity and specificity (see Kroenke, K., et al. (2001). The PHQ-9: validity of a brief depression severity measure. *J Gen Intern Med,* 16, 606-613.). PHQ-9 scores correspond to depression severity as set out in table 1.

TABLE 1

| PHQ-9 scores and depression severity | |
|---|---|
| PHQ-9 score | Depression severity |
| 0-4 | No depression |
| 5-9 | Mild depression |
| 10-14 | Moderate depression |

TABLE 1-continued

| PHQ-9 scores and depression severity | |
|---|---|
| PHQ-9 score | Depression severity |
| 15-19 | Moderately severe depression |
| 20-27 | Severe depression |

Generalised Anxiety Disorder (GAD 7)

The Generalised Anxiety Disorder (GAD 7) is a seven item self-administered questionnaire that is designed as a screening and severity measure for generalised anxiety disorder (GAD). The GAD-7 also has moderately good operating characteristics for three other common anxiety disorders, namely panic disorder, social anxiety disorder and post-traumatic stress disorder (see Spitzer, R. L., et al. (2006). A Brief Measure for Assessing Generalized Anxiety Disorder: The GAD-7. *Arch Intern Med.* 166, 1092-1097). GAD-7 scores correspond to anxiety severity as set out in table 2.

TABLE 2

| GAD-7 scores and anxiety severity | |
|---|---|
| PHQ-9 score | Anxiety severity |
| 0-4 | No anxiety |
| 5-9 | Mild anxiety |
| 10-14 | Moderate anxiety |
| 15-21 | Severe anxiety |

Stepped Care Model

The National Institute for Health and Clinical Excellence (NICE) recommends a range of psychological therapies to treat people with depression and anxiety disorders and bring them to recovery. It also recommends these therapies are used to provide a system of stepped care.

Stepped care has two principles:
treatment should always have the best chance of delivering positive outcomes while burdening the patient as little as possible, and
a system of scheduled review to detect and act on non-improvement must be in place to enable stepping up to more intensive treatments, stepping down where a less intensive treatment becomes appropriate and stepping out when an alternative treatment or no treatment become appropriate.

A recommended stepped care pathway is shown in Table 3 (see Improving Access to Psychological Therapies (IAPT) Programme, Department of Health (2012) *Guidance for Commissioning IAPT Training* 2012/13. Revised July 2012).

TABLE 3

| Stepped care model | | | |
|---|---|---|---|
| Step | Responsibility | Focus | Care |
| Step 1 | GP, practice nurse | Recognition | Assessment |
| Step 2 | Primary care team, primary care mental health worker | Mild depression/anxiety | Watchful waiting, guided self-help, computerised CBT, exercise, brief psychological interventions |
| Step 3 | Primary care team, primary care mental health worker | Moderate depression/anxiety | Medication, psychological interventions, social support |
| Step 3+ | | Moderately severe depression or severe depression/anxiety | |
| Step 4 | Mental health specialists, including crisis teams | Treatment-resistant, recurrent, atypical and psychotic depression and those at significant risk | Medication, complex psychological interventions, combined treatments |
| Step 5 | Inpatient care, crisis teams | Risk to life, sever self-neglect | Medication, combined treatments, ECT |

EXAMPLE

An example will now be described. The example involves a study of 747 patients. The average age of the patients was 37.9 years. 70% of the patients were female and 30% were male. The patients were referred to therapy for various reasons as set out in table 4.

TABLE 4

Reasons for therapy

| Disorder | Count |
| --- | --- |
| Adjustment disorders | 10 |
| Agoraphobia (with or without panic disorder) | 4 |
| Anxiety disorder, unspecified | 61 |
| Chronic intractable pain | 3 |
| Depressive episode | 210 |
| Disappearance and death of family member | 2 |
| Dysthymia | 3 |
| Eating disorders | 5 |
| Generalised anxiety disorder | 75 |
| Hypochondriacal disorder | 14 |
| Irritability and anger | 10 |
| Mental disorder, not otherwise specified | 16 |
| Mixed anxiety and depressive disorder | 122 |
| Obsessive-compulsive disorder | 33 |
| Panic disorder (episodic paroxysmal anxiety) | 78 |
| Post-traumatic stress disorder | 5 |
| Problems in relationship | 13 |
| Recurrent depressive order | 17 |
| Sexual dysfunction | 2 |
| Social phobias | 38 |
| Somatoform disorders | 3 |
| Specific (isolated) phobias | 12 |
| Blank/other | 11 |

132 patients were assigned to step 2, 472 patients were assigned to step 3, and 143 patients were assigned to step 3+.

All of the patients completed a course of therapy including one assessment and at least two therapy sessions.

The therapists were British Association of Cognitive and Behavioural (BABCP) accredited therapists. The therapists provide National Institute for Health and Care Excellence (NICE)-approved, disorder-specific interventions. The therapists are closely case managed to ensure adherence to clinical protocols. The therapists are mandated to attend clinical supervision on a regular basis. Clinical supervision is one of the primary methods used to develop and maintain clinical competence (see Milne, D. L (2009) *Evidence Based Clinical Supervision: Principles and Practice*. Oxford, Wiley/Blackwell).

Figure 9:
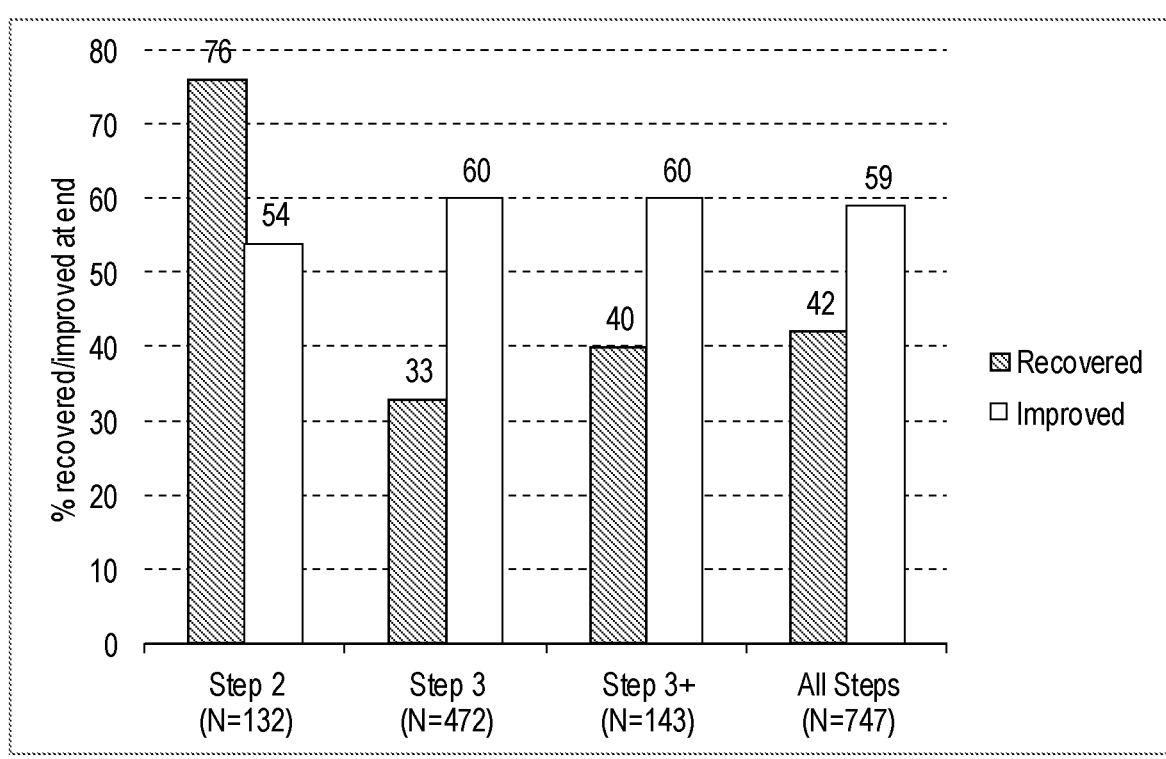
FIG. 9 is a graph of proportions of patients that statistically reliably recover or improve.
Figure 10:
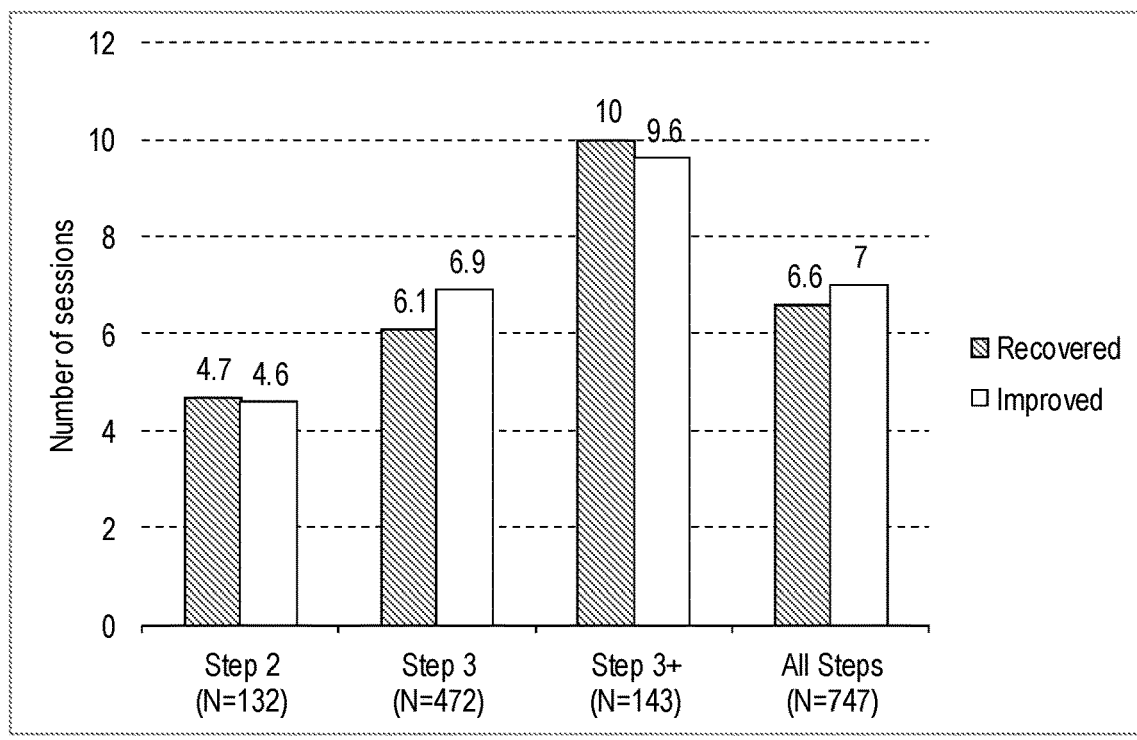
FIG. 10 is a graph of mean number of sessions for patients that statistically reliably recover or improve.
Figure 11:
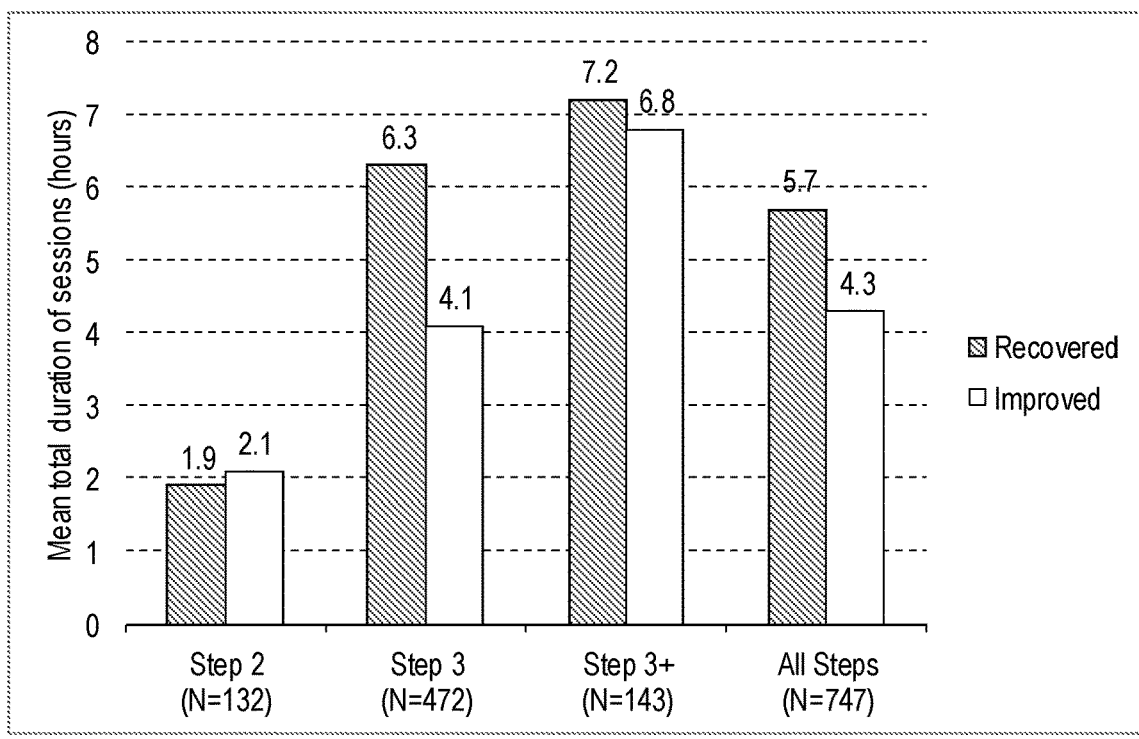
FIG. 11 is a graph of mean total duration of sessions for patients that statistically reliably recover or improve.

Referring to FIGS. 9 to 11, the results of the study will now be described.

FIG. 9 is a graph of the proportions of patients that statistically reliably recover or improve. Patients at step 2 have a 76% recovery rate and a 54% improvement rate. Patients at step 3 have a 33% recovery rate and a 60% improvement rate. Patients at step 3+ have a 40% recovery rate and a 60% improvement rate. Overall, patients have a 42% recovery rate and a 59% improvement rate.

FIG. 10 is a graph of mean number of sessions for patients that statistically reliably recover or improve. For patients at step 2 that recover, the mean number of sessions is 4.7. For patients at step 2 that improve, it is 4.6. For patients at step 3 that recover, the mean number of sessions is 6.1. For patients at step 3 that improve, it is 6.9. For patients at step 3+ that recover, the mean number of sessions is 10. For patients at step 3+ that improve, it is 9.6. Overall, for patients that recover, the mean number of sessions is 6.6, and for patients that improve, it is 7.

FIG. 11 is a graph of mean total duration of sessions for patients that statistically reliably recover or improve. For patients at step 2 that recover, the mean total duration of sessions is 1.9 hours. For patients at step 2 that improve, it is 2.1 hours. For patients at step 3 that recover, the mean total duration of sessions is 6.3 hours. For patients at step 3 that improve, it is 4.1 hours. For patients at step 3+ that recover, the mean total duration of sessions is 7.2 hours. For patients at step 3+ that improve, it is 6.8 hours. Overall, for patients that recover, the mean total duration of sessions is 5.7 hours, and for patients that improve, it is 4.3 hours.

Accordingly, the mean duration of sessions is between about 0.4 and 1.0 hours.

Without being limited to any particular explanation, the results described above may be explained by one or more of the following:

That people behave differently online. There is a widely cited disinhibition effect that occurs when people communicate using text via the internet (see Kessler, D. et al. (2009) Therapist-delivered internet psychotherapy for depression: a randomised controlled trial in primary care. *Lancet*, 374 ( ), 628-634). Consequently, people tend to disclose problems or concepts or beliefs more quickly and this enables treatment to more efficacious as the therapist is able to target key specific problems more quickly.

Learning being processed more effectively when people read and write (see Paivio, A. (1990) *Mental representations: A dual coding approach*. Oxford, Oxford University Press.). When people are presented with information aurally much of the content is lost as people are only likely to recall a small amount of what has been said (see Klinger, J., et al. (2011) Effects of visual and verbal presentation on cognitive load in vigilance, memory and arithmetic tasks. *Psychophysiology*, 48 ( ) 323-332). In addition, patients who use the system described above have secure access to all of their transcripts. Therefore, they are able to further consolidate any learning that has taken place each time they read through a transcript.

That the system described above reduces passive engagement with cognitive behavioural therapy. It has been found that for every hour of therapy a patient receives they are also on the system for a further hour. In that time they are reading transcripts, messaging their therapist, reviewing their goals and engaging in tasks.

That due to the non-instant messaging between sessions the therapist is able to positively reinforce new behaviours, encourage engagement in out of session tasks and provide addition support as required. This does not take place in face-to-face services where contact between sessions is strictly discouraged.

That the slower pace of the computer-based system encourages greater self-reflection. Self-reflection (for both therapist and patients) has been demonstrated to enhance learning and improve outcomes (see Bennett Levy, J. and Lee, N. K. (2014) Self practice and self-reflection in cognitive behaviour therapy training: what factors influence trainees' engagement and experience of benefit? *Behavioural and Cognitive Psychotherapy*, 42 (01), 48-64.).

That the computer-based system tends to increase the focus on the patient's primary problem and the collaborative focus on working towards the patient's goals. There is less social 'chat' in transcripts as patient and therapist structure their communication towards the agreed treatment plan.

That patients benefit from being able to access therapy from the privacy of their own home, thus reducing stigma, shame and embarrassment. Patients can be offered treatment at a time of day, or night, that suits them.

Modifications

It will be appreciated that many other modifications may be made to the embodiments hereinbefore described.

For example, the server 4 and second server 4' need not include the system modules described above. Furthermore, the functions described above as being performed by one system module may be performed by one or more other system modules.

The invention claimed is:

1. A method of treating depression and/or anxiety disorders, the method comprising:
   assigning a patient to a step of a stepped care model based on a depression severity determined by a PHQ-9 score and/or an anxiety severity determined by a GAD-7 score;
   administering a set of between about 5 and 10 psychological therapy sessions and/or a set of psychological therapy sessions with a total duration of between 1.5 and 7.5 hours based on the depression severity and/or the anxiety severity,
      wherein the said administering comprises: a therapist exchanging text-based instant messages with a remotely situated patient via a computer-based system during psychological therapy sessions, wherein the patient has a psychological condition and is remotely situated from the therapist; and
      wherein the psychological therapy sessions and/or the set of psychological therapy sessions comprises:
         for patients having mild depression and/or anxiety, a set of about 5 sessions and/or a set of sessions having a total duration of between 1.5 and 2.5 hours to achieve a recovery rate of at least about 76% and/or an improvement rate of at least about 54%;
         for patients having moderate depression and/or anxiety, a set of about 7 sessions and/or a set of sessions having a total duration of between 4 and 6.5 hours to achieve a recovery rate of at least about 33% and/or an improvement rate of at least about 60%; or
         for patients having severe depression and/or anxiety, a set of about 10 sessions and/or a set of sessions having a total duration of between 6.5 and 7.5 hours to achieve a recovery rate of at least about 40% and/or an improvement rate of at least about 60%;
   creating a transcript, via the computer-based system, of the text-based instant messages;
   saving the transcript in a database of the computer-based system;
   providing the transcript to the patient and/or the therapist through the computer-based system.

2. The method according to claim 1, wherein:
   patients having mild depression and/or anxiety correspond to patients at step 2 of the stepped care model;
   patients having moderate depression and/or anxiety correspond to patients at step 3 of the stepped care model; and/or
   patients having severe depression and/or anxiety correspond to patients at step 3+ of the stepped care model.

3. The method according to claim 1, wherein:
   recovery corresponds to a patient having a PHQ-9 score of less than 10 and/or a GAD-7 score of less than 8; and/or
   improvement corresponds to a patient having a PHQ-9 score that has decreased by at least 6 and/or a GAD-7 score that has decreased by at least 4 since before the set of sessions.

4. The method according to claim 1, wherein the psychological therapy sessions and/or the set of psychological therapy sessions have a session duration of between about 0.5 and 1 hour.

5. The method according to claim 1, comprising:
   allowing a patient, a therapist of the patient and/or a supervisor using the computer-based system to review messages previously sent between the patient and the therapist, and tasks previously completed by the patient.

6. The method according to claim 1, wherein the system corresponds to a computer-based system for providing the psychological therapy, comprising:
   a server comprising an apparatus for use in the computer-based system for providing the psychological therapy, the apparatus comprising: an access system configured to control access by users of remote devices to features and data, wherein the features of the apparatus comprise a therapy system, wherein the users comprise patients, therapists and supervisors; and a therapy system configured to enable text-based instant messages to be sent between the patients and the therapists; wherein the access system is configured to allow the patients to the messages sent and received by the patient, the therapists to retrieve messages sent and received by the therapist, and the supervisors to retrieve messages sent and received by particular patients and/or therapists;
   at least one network; and
   a plurality of devices configured to communicate with the server via the at least one network.

7. The method according to claim 1, comprising:
   text mining, via the computer-based system, the text-based instant messages;
   determining at least one feature of the text-based instant messages based on the text mining; and
   determining a characteristic of the patient based on (a) the at least one feature and (b) a severity measure of the psychological condition, wherein the characteristic relates to a predicted outcome of therapy, a risky behavior by the patient, and/or a predicted drop-out by the patient.

8. The method according to claim 1, wherein communication in the psychological therapy sessions consists of the text-based instant messages.

9. The method according to claim 7 further comprising:
   alerting the therapist and/or the supervisor based on the characteristic of the patient.

10. A method of treating depression and/or anxiety disorders, the method comprising:
    assigning a patient to a step of a stepped care model based on a depression severity determined by a PHQ-9 score and/or an anxiety severity determined by a GAD-7 score;
    administering a set of between about 5 and 10 psychological therapy sessions and/or a set of psychological therapy sessions with a total duration of between 1.5 and 7.5 hours based on the depression severity and/or the anxiety severity,
       wherein the said administering comprises: a therapist exchanging text-based instant messages with a remotely situated patient via a computer-based system during psychological therapy sessions, wherein the patient has a psychological condition and is remotely situated from the therapist; and wherein the psychological therapy sessions and/or the set of psychological therapy sessions comprises:

for patients having mild depression and/or anxiety, a set of about 5 sessions and/or a set of sessions having a total duration of between 1.5 and 2.5 hours to achieve a recovery rate of at least about 76% and/or an improvement rate of at least about 54%;

for patients having moderate depression and/or anxiety, a set of about 7 sessions and/or a set of sessions having a total duration of between 4 and 6.5 hours to achieve a recovery rate of at least about 33% and/or an improvement rate of at least about 60%; or for patients having severe depression and/or anxiety, a set of about 10 sessions and/or a set of sessions having a total duration of between 6.5 and 7.5 hours to achieve a recovery rate of at least about 40% and/or an improvement rate of at least about 60%.

11. The method according to claim 10, wherein communication in the psychological therapy sessions consists of the text-based instant messages.

12. The method according to claim 10, comprising:

text mining, via the computer-based system, the text-based instant messages;

determining at least one feature of the text-based instant messages based on the text mining; and determining a characteristic of the patient based on (a) the at least one feature and (b) a severity measure of the psychological condition, wherein the characteristic relates to a predicted outcome of therapy, a risky behavior by the patient, and/or a predicted drop-out by the patient.

13. The method according to claim 12 further comprising:

alerting the therapist and/or the supervisor based on the characteristic of the patient.

* * * * *